United States Patent
Misske et al.

(10) Patent No.: US 11,028,040 B2
(45) Date of Patent: Jun. 8, 2021

(54) METHODS FOR PRODUCING (METH)ACRYLIC ACID NORBORNYL ESTERS

(71) Applicant: BASF SE, Ludwigshafen am Rhein (DE)

(72) Inventors: Andrea Misske, Ludwigshafen am Rhein (DE); Christoph Fleckenstein, Ludwigshafen am Rhein (DE); Friederike Fleischhaker, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 36 days.

(21) Appl. No.: 16/480,703

(22) PCT Filed: Jan. 22, 2018

(86) PCT No.: PCT/EP2018/051381
§ 371 (c)(1),
(2) Date: Jul. 25, 2019

(87) PCT Pub. No.: WO2018/138025
PCT Pub. Date: Aug. 2, 2018

(65) Prior Publication Data
US 2020/0407309 A1     Dec. 31, 2020

(30) Foreign Application Priority Data

Jan. 27, 2017 (EP) ..................... 17153566

(51) Int. Cl.
| | | |
|---|---|---|
| C07C 67/62 | (2006.01) | |
| C07C 67/05 | (2006.01) | |
| C07C 67/04 | (2006.01) | |
| C07C 67/54 | (2006.01) | |

(52) U.S. Cl.
CPC ............. *C07C 67/62* (2013.01); *C07C 67/05* (2013.01); *C07C 67/54* (2013.01)

(58) Field of Classification Search
CPC .......... C07C 67/62; C07C 67/54; C07C 67/05
See application file for complete search history.

(56) References Cited

U.S. PATENT DOCUMENTS

| | | |
|---|---|---|
| 9,562,054 B2 | 2/2017 | Misske et al. |
| 10,370,383 B2 | 8/2019 | Misske et al. |
| 2018/0036940 A1 | 2/2018 | Fleischhaker et al. |
| 2018/0036954 A1 | 2/2018 | Fleischhaker et al. |
| 2018/0043436 A1 | 2/2018 | Chen et al. |
| 2018/0201712 A1 | 7/2018 | Licht et al. |
| 2018/0201722 A1 | 7/2018 | Fleischhaker et al. |
| 2019/0169346 A1 | 6/2019 | Misske et al. |

FOREIGN PATENT DOCUMENTS

| | | |
|---|---|---|
| DE | 1954548 A1 | 5/1971 |
| JP | H03-148239 A | 6/1991 |
| WO | WO-2016165979 A1 | 10/2016 |
| WO | WO-2017102675 A1 | 6/2017 |

OTHER PUBLICATIONS

Mamedov et al, Russian Journal of Organic Chemistry, Synthesis of Bi- and Tricyclic Acrylates in the Presence of Boron Trifluoride Etherate, 2010, vol. 46, No. 5, pp. 628-630. (Year: 2010).*
European Search Report for EP Patent Application No. 17153566.9, dated Jul. 27, 2017.
Müller, E., et al., "Liquid—Liquid Extraction—Apparatus", Ullmann's Encyclopedia of Industrial Chemistry, 2005, pp. 1-54.
Mamedov, et al., "Synthesis of acetic-methacrylic acid diesters of norbornane-2,5-diol and (2-hydroxynorborn-5-yl)methanol", Russian Journal of Applied Chemistry, vol. 83, Issue 11, Nov. 2010, pp. 1978-1981.
M. K. Mamedov et al., "Synthesis of Bi- and Tricyclic Acrylates in the Presence of Boron Trifluoride Etherate", Russian Journal of Organic Chemistry, vol. 46, No. 5, pp. 628-630, 2010.
International Search Report for PCT/EP2018/051381 dated Apr. 4, 2018.
Written Opinion of the International Searching Authority for PCT/EP2018/051381 dated Apr. 4, 2018.

* cited by examiner

*Primary Examiner* — Paul A Zucker
(74) *Attorney, Agent, or Firm* — Faegre Drinker Biddle & Reath LLP

(57) ABSTRACT

A method for preparing norbornyl (meth)acrylate by reacting norbornene with (meth)acrylic acid in the presence of boron trifluoride as catalyst, wherein a) boron trifluoride is initially charged in (meth)acrylic acid or an organic solvent, b) the initial charge is heated to a temperature of 75 to 110° C., c) norbornene is added or a mixture comprising norbornene and (meth)acrylic acid is added and d) the norbornyl (meth)acrylate obtained is isolated from the reaction mixture.

14 Claims, No Drawings

METHODS FOR PRODUCING (METH)ACRYLIC ACID NORBORNYL ESTERS

CROSS-REFERENCE TO RELATED APPLICATIONS

This application is a national stage application (under 35 U.S.C. § 371) of PCT/EP2018/051381, filed Jan. 22, 2018, which claims benefit of European Application No. 17153566.9, filed Jan. 27, 2017, both of which are incorporated herein by reference in their entirety.

The present invention relates to the preparation of norbornyl (meth)acrylate. The methods according to the invention involve reacting norbornene and (meth)acrylic acid in the presence of boron trifluoride.

Norbornyl (meth)acrylate is used by way of example for producing copolymers. Copolymers comprising norbornyl (meth)acrylate as comonomer in copolymerized form are used by way of example as a constituent of curable compositions. Curable compositions are used in adhesives, sealants, printing inks, jettable printing inks and also in coatings for electronics, in coatings in the field of the automotive industry, and generally in the industrial sector.

Methods for preparing norbornyl (meth)acrylate from (meth)acrylic acid and norbornene are known to those skilled in the art from the prior art. In general, (meth)acrylic acid is added to norbornene in the presence of an acidic catalyst. Suitable acidic catalysts are by way of example Lewis acids such as boron trifluoride or complexes thereof.

The addition of acrylic acid to norbornene in the presence of boron trifluoride diethyl etherate is described in the Russian Journal of Organic Chemistry (2010, Vol. 46, pages 628-630). According to the example disclosed, norbornene, acrylic acid and boron trifluoride diethyl etherate are initially charged and heated. Norbornyl (meth)acrylate is subsequently isolated from the reaction mixture with a yield of 80% by fractional distillation.

The object was to make available an improved method for preparing norbornyl (meth)acrylate. The improved method was to make it possible to prepare norbornyl (meth)acrylate with higher selectivity, yield and purity. It was furthermore desirable for norbornyl (meth)acrylate to be able to be isolated with high purity and yield with only little expense. It is therefore advantageous, for example, if norbornyl (meth)acrylate can be isolated from the reaction mixture with high purity and yield, without fractional distillation.

The object is achieved by a method for preparing norbornyl (meth)acrylate by reacting norbornene with (meth)acrylic acid in the presence of boron trifluoride as catalyst, wherein
a) boron trifluoride is initially charged in (meth)acrylic acid,
b) the initial charge is heated to a temperature of 75 to 110° C.,
c) norbornene is added and
d) the norbornyl (meth)acrylate obtained is isolated from the reaction mixture.

The object is also achieved by a method for preparing norbornyl (meth)acrylate by reacting norbornene with (meth)acrylic acid in the presence of boron trifluoride as catalyst, wherein
a) boron trifluoride is initially charged in an organic solvent,
b) the initial charge is heated to a temperature of 75 to 110° C.,
c) a mixture comprising norbornene and (meth)acrylic acid is added and
d) the norbornyl (meth)acrylate obtained is isolated from the reaction mixture.

Norbornyl (meth)acrylate is norbornyl acrylate or norbornyl methacrylate.

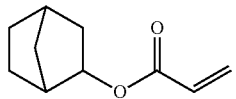 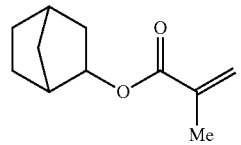

(Meth)acrylic acid is acrylic acid or methacrylic acid. The (meth)acrylic acid used in the methods according to the invention is generally very pure. Very pure (meth)acrylic acid has a purity of at least 95 percent by weight. It is preferable for the (meth)acrylic acid used in the methods according to the invention to have a purity of at least 97 percent by weight and further preferably a purity of at least 99 percent by weight.

In the methods according to the invention, (meth)acrylic acid is used in an amount of 100 to 1000 mole percent, preferably 105 to 750 mole percent and particularly preferably 110 to 250 mole percent, based on the amount of norbornene.

Even though (meth)acrylic acid can be used in the methods according to the invention without a stabilizer, it is generally preferable for the (meth)acrylic acid used to comprise a stabilizer or a mixture of various stabilizers.

A stabilizer, or a mixture of various stabilizers, generally serves to inhibit the polymerization of (meth)acrylic acid or of the corresponding esters.

The amount of stabilizer present in the (meth)acrylic acid used is generally guided by the nature of the stabilizer used, or the nature of the stabilizers used if a mixture of various stabilizers is used. In general, the amount of stabilizer present in the (meth)acrylic acid used is 50 to 1000 ppm, preferably 100 to 800 ppm and further preferably 150 to 300 ppm.

Stabilizers that inhibit the polymerization of (meth)acrylic acid are known to those skilled in the art or are revealed to them from their general technical knowledge. Known stabilizers are for example copper (meth)acrylates, copper dithiocarbamates, phenothiazines, phenolic compounds, N-oxyls, phenylenediamines, nitroso compounds, ureas or thioureas. These stabilizers can be used individually or as any desired mixture. Preferred stabilizers are phenothiazines, phenolic compounds, N-oxyls or any desired mixtures of these.

Phenothiazines may by way of example be phenothiazine, bis(α-methylbenzyl)phenothiazine, 3,7-dioctylphenothiazine, bis(α-dimethylbenzyl)phenothiazine or any desired mixture of these.

Phenolic compounds may for example be hydroquinone, hydroquinone monomethyl ether, such as para-methoxyphenol (MEHQ), pyrogallol, catechol, resorcinol, phenol, cresol, 2,4-dimethyl-6-tert-butylphenol, 2,6-di-tert-butyl-para-cresol or any desired mixture of these. Preferred phenolic compounds are para-methoxyphenol (MEHQ), 2,4-dimethyl-6-tert-butylphenol, 2,6-di-tert-butyl-para-cresol or any desired mixture of these. Para-methoxyphenol (MEHQ) is particularly preferred.

N-oxyls may for example be di-tert-butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidinoxyl, 4-hydroxy-2,2,6,6-tetramethylpiperidinoxyl, 4,4',4"-tris-1-(2,2,6,6-tetramethylpiperidinoxyl)phosphites or any desired mixture of these.

It is particularly preferable for the (meth)acrylic acid used in the methods according to the invention to be stabilized with para-methoxyphenol (MEHQ). The amount of MEHQ in the (meth)acrylic acid used in the methods according to the invention is preferably 150 to 300 ppm.

Norbornene of very high purity is used in the methods according to the invention. In general, norbornene with a purity of at least 90 percent by weight is used. It is preferable for norbornene with a purity of at least 95 percent by weight and further preferably with a purity of at least 97 percent by weight to be used. The obtaining of norbornene of appropriate purity is known to those skilled in the art or is revealed to them from their general technical knowledge.

According to the methods according to the invention, boron trifluoride is initially charged in step a) in (meth)acrylic acid or in an organic solvent. In general, (meth)acrylic acid or the organic solvent are in the liquid phase and boron trifluoride is added to the liquid phase present. It is preferable for boron trifluoride to be initially charged in (meth)acrylic acid or in an organic solvent at a temperature of 15 to 50° C. It is further preferable for boron trifluoride to be initially charged in (meth)acrylic acid or in an organic solvent at a temperature of 20 to 35° C.

Boron trifluoride is preferably initially charged in (meth)acrylic acid or in an organic solvent in the presence of oxygen. Therefore, boron trifluoride may, by way of example, be initially charged, in the presence of an oxygen-containing gas such as air, lean air or dried air, in (meth)acrylic acid or in an organic solvent. In the context of the methods according to the invention, the presence of oxygen generally proves to be advantageous since the inhibition of the polymerization of the (meth)acrylic acid used and/or of the norbornyl (meth)acrylate prepared is influenced positively as a result.

Boron trifluoride is generally supplied in gaseous form or as a complex to the initially charged (meth)acrylic acid or to the initially charged organic solvent. If boron trifluoride is supplied in gaseous form, it is advantageous for boron trifluoride to be introduced into the initially charged (meth)acrylic acid or into the initially charged organic solvent. Introduction may take place, for example, through one or more immersion pipes or nozzles that are corrosion resistant with respect to boron trifluoride. By introducing gaseous boron trifluoride into the initially charged (meth)acrylic acid or into the initially charged organic solvent, complex formation may occur. If boron trifluoride is supplied as a complex to the initially charged (meth)acrylic acid or to the initially charged organic solvent, transcomplexation may occur.

Examples of boron trifluoride complexes are boron trifluoride etherates, boron trifluoride acetonitrile complexes, boron trifluoride hydrates, boron trifluoride carboxylic acid complexes such as boron trifluoride acetic acid complexes or boron trifluoride (meth)acrylic acid complexes, or any desired mixtures of these complexes. Preference is given to boron trifluoride etherates. Boron trifluoride etherates may for example be boron trifluoride dimethyl etherate, boron trifluoride diethyl etherate, boron trifluoride tetrahydrofuran complexes or any desired mixtures of these. Preference among the boron trifluoride etherates is given to boron trifluoride dimethyl etherate and/or boron trifluoride diethyl etherate. Particular preference is given to boron trifluoride dimethyl etherate.

If boron trifluoride is supplied as a complex to the initially charged (meth)acrylic acid or to the initially charged organic solvent, it may be the case that the complex is dissolved in a solvent. The solvent is usually the compound that was used for the complex formation.

In the methods according to the invention, boron trifluoride is used in an amount of 0.1 to 5 mole percent, preferably in an amount of 0.2 to 2.5 mole percent and further preferably in an amount of 0.5 to 1.5 mole percent, based on the amount of norbornene. Therefore, by way of example, boron trifluoride may be used in an amount of 0.6, 0.7, 0.8, 0.9, 1.0, 1.1, 1.2, 1.3 or 1.4 mole percent, based on the amount of norbornene.

Suitable as organic solvent, in which boron trifluoride is initially charged, are in principle all organic solvents that do not undergo any undesired reactions with the starting materials, the catalyst and the products and lead to undesired formation of by-products. It is advantageous if the boiling point of the organic solvent is above 75° C. at standard pressure.

As organic solvent, it is possible to use polar aprotic solvents, nonpolar aprotic solvents, (meth)acrylic acid, norbornyl (meth)acrylate or any desired mixture of these. Polar aprotic solvents may for example be nitriles, such as acetonitrile, nitro compounds, such as nitromethane, sulfoxides, such as dimethyl sulfoxide, lactams, such as N-methyl-2-pyrrolidone, tertiary carboxamides, such as dimethylformamide, ketones, dichloromethane, trichloromethane or any desired mixture of these. Nonpolar aprotic solvents may for example be ethers, such as alkyl ethers, toluene or any desired mixture of these. Alkyl ethers may for example be dimethyl ether, diethyl ether, methyl tert-butyl ether, tetrahydrofuran, 1,4-dioxane or any desired mixture of these. The use of norbornene as organic solvent has not been found to be advantageous. Preferred organic solvents are (meth)acrylic acid, norbornyl (meth)acrylate, ethers, where 1,4-dioxane is preferred, or any desired mixture of these.

A stabilizer or a mixture of various stabilizers may additionally be supplied to the initially charged (meth)acrylic acid or to the initially charged organic solvent. If a stabilizer or a mixture of various stabilizers is additionally supplied to the initially charged (meth)acrylic acid or to the initially charged organic solvent, this generally takes place before boron trifluoride is supplied to the initially charged (meth)acrylic acid or to the initially charged organic solvent.

The amount of stabilizer that is additionally supplied to the initially charged (meth)acrylic acid or to the initially charged organic solvent is guided by the nature of the stabilizer or by the nature of the mixture of various stabilizers. In general, the amount of stabilizer that is additionally supplied is 0.005 to 0.15 and preferably 0.05 to 0.15 mole percent, based on the amount of the (meth)acrylic acid used in the methods according to the invention.

The abovementioned stabilizers may be used as stabilizer. In general, it is advantageous to use the stabilizer or the mixture of various stabilizers that are already present in the (meth)acrylic acid used in the methods according to the invention. It is accordingly preferable for MEHQ to be additionally supplied to the initially charged (meth)acrylic acid or to the initially charged organic solvent.

In preferred method configurations, boron trifluoride is initially charged in (meth)acrylic acid, norbornyl (meth)acrylate or in 1,4-dioxane. Boron trifluoride is initially charged here in gaseous form or as a complex, preferably as the dimethyl etherate or as the diethyl etherate. The temperature at which boron trifluoride is initially charged in (meth)acrylic acid, norbornyl (meth)acrylate or in 1,4-dioxane is 15 to 50° C. here. The temperature may for example be 18, 20, 22, 24, 26, 28, 30, 32 or 35° C.

In further-preferred method configurations, boron trifluoride is initially charged in (meth)acrylic acid, norbornyl (meth)acrylate or in 1,4-dioxane. Boron trifluoride is initially charged here in gaseous form or as a complex, preferably as the dimethyl etherate or as the diethyl etherate, in an amount of 0.5 to 1.5 mole percent, based on the amount of norbornene. The temperature at which boron trifluoride is initially charged in (meth)acrylic acid, norbornyl (meth)acrylate or in 1,4-dioxane is 15 to 50° C. here. The temperature may for example be 18, 20, 22, 24, 26, 28, 30, 32 or 35° C.

The methods according to the invention can be performed in reactors known to those skilled in the art. As reactors, use may for example be made of stirred tank reactors, loop reactors, tubular reactors, or any desired combinations of these. The reactors are in general made from metallic material, stainless steel being preferred.

The reactors may be reactors with jacket heating and/or internal heating coils. The reactors may also be reactors having external heat exchangers and natural or forced circulation (using a pump). Mixing in the reactors may take place by way of stirring apparatuses and/or by feeding in a gas, preferably an oxygen-containing gas.

The methods according to the invention can be performed continuously or batchwise, with batchwise execution being preferred. In general, preference is given to reactors that are suitable for a batchwise reaction regime, for example stirred tank reactors. A plurality of reactors, preferably stirred tank reactors, may be connected in series and/or in parallel. When selecting suitable reactors and the interconnection thereof, those skilled in the art can be guided by their general technical knowledge and practical considerations.

In step b) of the methods according to the invention, the initial charge is heated. The initial charge is heated to a temperature of 75 to 110° C., preferably 80 to 105° C. and further preferably to a temperature of 85 to 100° C.

Heating of the initial charge generally takes place in the presence of oxygen. Thus, by way of example, oxygen-containing gases such as air, lean air or dried air can be fed to the initial charge during the heating. The oxygen-containing gas that is fed to the initial charge during the heating is generally fed to the gas space above the initial charge. The oxygen-containing gas can, however, also be fed directly into the initial charge, by way of example through one or more immersion pipes or nozzles, through which the oxygen-containing gas flows out.

In step c) of the methods according to the invention, norbornene or a mixture comprising norbornene and (meth)acrylic acid is added to the heated initial charge. If norbornene or a mixture comprising norbornene and (meth)acrylic acid is added, the initial charge has a temperature of 75 to 110° C., preferably 80 to 105° C. and further preferably a temperature of 85 to 100° C.

Norbornene or a mixture comprising norbornene and (meth)acrylic acid can be added to the heated initial charge in one go or gradually. The gradual addition can take place continuously or discontinuously. In general, norbornene or a mixture comprising norbornene and (meth)acrylic acid is added to the heated initial charge continuously.

The rate of addition is guided by the evolution of heat of the reaction and should be chosen such that the temperature of the initial charge increases by not more than 20° C., preferably by not more than 10° C. and particularly preferably by not more than 5° C.

Continuous addition of norbornene or a mixture comprising norbornene and (meth)acrylic acid can be performed by conveying means known to those skilled in the art. Thus, continuous addition can be performed by way of example via a screw, a conveyor belt, a pump, a conveying drum or any desired combination of these.

Norbornene can be added to the heated initial charge in solid or liquid form. Of course, those skilled in the art match the choice of a suitable conveying means to the nature of the substance or substance mixture to be conveyed. Preference is given to adding norbornene to the heated initial charge in liquid form. To this end, solid norbornene is melted. Some of the heat required for this may be obtained by way of example by thermal integration with the heated initial charge, for example through waste heat from the heated initial charge. The liquid norbornene may then be added to the heated initial charge via heated lines and/or conveying means.

A mixture comprising norbornene and (meth)acrylic acid is generally added to the heated initial charge in liquid form. To this end, norbornene may be dissolved in liquid (meth)acrylic acid in solid or liquid form. In addition to norbornene and (meth)acrylic acid, the mixture may also comprise one or a mixture of various stabilizers. Even though, in general, (meth)acrylic acid is used which already comprises one or a mixture of various stabilizers, it is advantageous to additionally supply a stabilizer or mixture of various stabilizers to the mixture. If a stabilizer or a mixture of various stabilizers is additionally supplied to the mixture comprising norbornene and (meth)acrylic acid, it is advantageous to use a stabilizer or a mixture of various stabilizers that are already present in the (meth)acrylic acid.

The amount of stabilizer that is additionally supplied to the mixture comprising norbornene and (meth)acrylic acid is guided by the nature of the stabilizer or by the nature of the mixture of various stabilizers. In general, the amount of stabilizer that is additionally supplied to the mixture comprising norbornene and (meth)acrylic acid is 0.005 to 0.15 and preferably 0.05 to 0.15 mole percent, based on the amount of (meth)acrylic acid present in the mixture.

The abovementioned stabilizers can be used as stabilizer, with MEHQ being preferred.

The addition of norbornene or a mixture comprising norbornene and (meth)acrylic acid to the heated initial charge advantageously takes place in the presence of oxygen. To this end, an oxygen-containing gas can be fed into the heated initial charge, into the gas space above the heated initial charge, into the addition lines and/or into the feed stream of norbornene or of a mixture comprising norbornene and (meth)acrylic acid. If the oxygen-containing gas is fed into the heated initial charge or into the feed stream of norbornene or of a mixture comprising norbornene and (meth)acrylic acid, this may by way of example take place via one or more immersion pipes or nozzles, through which the oxygen-containing gas flows out.

After reacting the deficient component, generally norbornene, the norbornyl (meth)acrylate obtained is isolated from the reaction mixture in step d) of the methods according to the invention. The reaction mixture is the mixture that is obtained after steps a) to c) of the methods according to the invention.

Norbornyl (meth)acrylate can be isolated from the reaction mixture by extraction and/or distillative separation (distillation) of the lower-boiling compounds.

If norbornyl (meth)acrylate is isolated by extraction, this can take place via one or more extraction steps.

In general, the reaction mixture is admixed for this purpose with an aqueous solution of a base, and the phases are subsequently separated. The concentration of the aqueous base solution corresponds to the usual concentrations that are used for extraction purposes and can vary over a wide range. Advantageous concentrations can be determined by those skilled in the art by few routine experiments, or are revealed to them from their general technical knowledge or on the basis of practical considerations.

A base is for example sodium hydroxide, potassium hydroxide, sodium hydrogencarbonate, potassium hydrogencarbonate, calcium hydroxide, ammonia, potassium carbonate, or any desired mixtures of these. Preferably, the base is sodium hydroxide. The aqueous solution of a base may additionally comprise a further salt. A further salt is for example sodium chloride, potassium chloride, ammonium chloride, ammonium sulfate, or any desired mixtures of these. It is preferable for the further salt to be sodium chloride. The amount of the further salt corresponds to the usual amounts that can be used for extraction purposes. Advantageous amounts can be determined by those skilled in the art by few routine experiments, or are revealed to them from their general technical knowledge or on the basis of practical considerations.

The addition of the aqueous solution of a base takes place in a manner such that the temperature of the reaction mixture does not rise above 40° C. and the pH after adding the aqueous solution of a base is 10 to 14. The heat of neutralization is optionally removed by cooling the reaction mixture, for example by internal cooling coils or by means of jacket cooling. The vessel in this the reaction mixture is admixed with an aqueous solution of a base should therefore be designed correspondingly.

An organic solvent which is sparingly soluble in water may additionally be added to the reaction mixture. This may serve, by way of example, to better control the temperature profile when adding an aqueous solution of a base. An organic solvent that is sparingly soluble in water has a solubility in water of less than 10 g/l of water at 20° C., preferably less than 1 g/l of water at 20° C.

The ratio of reaction mixture:aqueous solution of a base can be varied over broad ranges. Advantageous ratios can be determined by those skilled in the art by few routine experiments, or are revealed to them from their general technical knowledge or on the basis of practical considerations.

A subsequent wash may be advantageous for removing traces of base and/or salt from the reaction mixture after phase separation. To this end, the reaction mixture may be treated with a wash liquid. A wash liquid is for example water. It may be advantageous for water, as wash liquid, to comprise a salt. A salt is for example sodium chloride, potassium chloride, ammonium chloride, sodium sulfate, aluminum sulfate, or any desired mixtures of these. The amount of salt can be varied over wide ranges. Advantageous amounts can be determined by those skilled in the art by few routine experiments, or are revealed to them from their general technical knowledge or on the basis of practical considerations.

In process engineering terms, for an extraction in the methods according to the invention, it is possible to use any extraction and washing methods and apparatuses known per se, for example those described in Ullmann's Encyclopedia of Industrial Chemistry, 6th ed., 1999 Electronic Release, chapter "Liquid-Liquid Extraction-Apparatus". For example, these may be single-stage or multistage, preferably single-stage, extractions and also extractions in cocurrent or countercurrent mode. Vessels which are suitable for the extraction are by way of example stirred vessels, columns or mixer-settler apparatuses.

The organic phase obtained after extraction, which comprises norbornyl (meth)acrylate, is optionally admixed with a stabilizer or a mixture of various stabilizers, in order to set an advantageous stabilizer concentration. The stabilizer concentration to be set depends in general on the particular specification of the end product and for commercially obtainable alkyl (meth)acrylates is in the range from 15 to 200 ppm. It may thus be advantageous to set a stabilizer concentration of 30, 50, 80, 100, 120, 150 or 180 ppm.

As stabilizers, in general phenolic compounds, such as 2,6-di-tert-butyl-4-methylphenol, 6-tert-butyl-2,4-dimethylphenol, hydroquinone, hydroquinone monomethyl ether or any desired mixture of these, are used. Hydroquinone monomethyl ether (MEHQ) is preferred.

After extraction, the organic phase, comprising norbornyl (meth)acrylate and optionally a stabilizer or a mixture of various stabilizers, can be further worked up in accordance with methods known to those skilled in the art, in order to obtain norbornyl (meth)acrylate. To this end, norbornyl (meth)acrylate, optionally together with the stabilizer or mixture of various stabilizers, can be separated off from the other constituents of the organic phase by way of example by distillation or stripping. The separated-off constituents of the organic phase, preferably the organic solvent, may for example be used again in the extraction.

If norbornyl (meth)acrylate is isolated by distillative separation of the lower-boiling compounds, this can take place in one or more distillation steps. In general, unreacted (meth)acrylic acid, optionally the organic solvent, boron trifluoride and other more volatile compounds are separated off from the reaction mixture by distillation. Norbornyl (meth)acrylate remains behind as bottoms fraction. The methods according to the invention minimize the formation of higher-boiling by-products, for example by-products formed by dimerization of (meth)acrylic acid, as a result of which fractional distillation of the norbornyl (meth)acrylate can be dispensed with.

Since norbornyl (meth)acrylate does not itself need to be isolated by distillation and accumulates as bottoms fraction with high purity, the distillation of the lower-boiling compounds can take place in simple apparatuses.

Suitable apparatuses for distillative separation of the lower-boiling compounds are in general all apparatuses for distillative separation of reaction mixtures comprising liquid components. Suitable apparatuses include distillation columns such as tray columns, which may be equipped with bubble-cap trays, sieve plates, sieve trays, structured packings or random packings, or spinning band column evaporators such as thin film evaporators, falling film evaporators, forced circulation evaporators, Sambay evaporators etc., and combinations thereof.

One or more distillation steps can be connected in succession. The distillation steps can take place in identical or different apparatuses.

When choosing suitable temperature and pressure ranges for distillative separation of the lower-boiling compounds, those skilled in the art can be guided by the physical conditions of the separation task (for example vapor pressure curves) and by their general technical knowledge and by practical considerations.

It is possible to combine extraction and distillation. Thus, the reaction mixture may by way of example firstly be subjected to extraction and subsequently to distillation, or vice versa. When combining extraction and distillation it is generally preferable to subject the reaction mixture firstly to distillation, in order to separate off the lower-boiling compounds. The bottoms fraction, obtained after separating off the lower-boiling compounds and comprising norbornyl (meth)acrylate, can then be further worked up by extraction.

The methods according to the invention, make it possible to produce norbornyl (meth)acrylate with high purity and in high yield. Thus, norbornyl (meth)acrylate can be isolated with a purity of at least 99 percent by weight. The yield of norbornyl (meth)acrylate in this case is at least 90 percent.

Advantageously, norbornyl (meth)acrylate does not itself need to be subjected to any distillative or rectificative purification in order to achieve the high purity. As already stated, norbornyl (meth)acrylate can be isolated with high purity by extraction and/or distillative separation of the lower-boiling compounds. This has the further advantage that the preparation and isolation of norbornyl (meth)acrylate can take place in relatively simple apparatuses. The thermal stress of norbornyl (meth)acrylate during the isolation is also reduced, as a result of which the formation of by-products can be minimized.

In order to reduce the color number of the norbornyl (meth)acrylate prepared by the methods according to the invention, it may be advantageous for norbornyl (meth)acrylate to be distilled. To this end, norbornyl (meth)acrylate can be isolated for example directly by distillation from the reaction mixture. If norbornyl (meth)acrylate was isolated by extraction and/or distillative separation of the lower-boiling compounds, the norbornyl (meth)acrylate thus obtained can also be subjected to distillation.

The norbornyl (meth)acrylate prepared by the methods according to the invention is especially suitable, on account of its high purity, for the preparation of homo- or copolymers.

Copolymers comprising norbornyl (meth)acrylate in copolymerized form are suitable as a constituent of curable compositions. Such curable compositions are suitable for example for use in pressure-sensitive adhesives, printing inks, especially screen-printing inks, jettable printing inks and also for paints, especially for primers, topcoats, basecoats or clearcoats. Such curable compositions are also suitable for uses in coatings for LCD and LED displays, in coatings for glass bottles, especially beer bottles, in coatings for plastic bottles, especially shampoo bottles, in coatings for thermal paper and in coatings for reflective films.

Unless stated to the contrary, all indications in ppm relate to the respective total weight.

All indications in percentage by weight (% by weight), unless stated to the contrary, relate to the respective total weight.

The determination of the purity of the norbornyl (meth)acrylate was performed by gas chromatography as indicated in the experimental section.

Experimental Section:

The purity was determined by means of gas chromatography. As solvent for the samples, dichloromethane from Aldrich was used, purity 99.8%.

As apparatus, a gas chromatograph from Hewlett Packard (7890B) with FID detector and 50 m CP-Sil 5 CB 50 m*0.25 mm*0.25 μm column from Agilent was used. The following was set as temperature program: 60° C. start, then with 15° C./min to 280° C., 1 min at 280° C., total run time 15.7 min.

The Hazen color number was measured using a color number measuring instrument from Hach Lange (LICO 620) and calculated for standard illuminant C and 2° standard observer corresponding to DIN 5033.

Starting Materials Used;

| | Source | Purity | Stabilization |
|---|---|---|---|
| methacrylic acid, pure | BASF | >99.5% | 200 ± 20 ppm MEHQ |
| acrylic acid, pure | BASF | >99.5% | 200 ± 20 ppm MEHQ |
| norbornene | Aldrich | >99% | |
| BF3 dimethyl etherate | Aldrich | 59-61% BF3 | |
| MEHQ | Aldrich | >99% | |
| dioxane | Aldrich | >99.5% | |
| DCM | BASF | >98% | |
| NaOH | BerndKraft | ultrapure | |
| NaCl | BerndKraft | >99% | |

EXAMPLE 1: NORBORNYL ACRYLATE WITH INITIAL CHARGE OF NORBORNYL ACRYLATE 5 ml of norbornyl acrylate were initially charged in a 250 ml four-neck round-bottom flask with reflux condenser, magnetic stirrer, thermometer, dropping funnel and air inlet. 0.5 ml of boron trifluoride dimethyl etherate was added. A solution of 40 g of norbornene, 0.1 g of MEHQ and 61.5 g of acrylic acid was added dropwise with introduction of air (1 l/h), stirring (280 rpm) and heating, such that the internal temperature was 90-92° C. The mixture was stirred at temperature for a further 1 h. The reaction mixture that had cooled to room temperature was admixed with 300 ml of dichloromethane and with 200 ml of 12.5% NaOH solution and extracted. The phases were separated, the organic phase was extracted once more with 100 ml of 12.5% NaOH solution and concentrated after phase separation. 71.6 g of product (94.5% yield) were obtained with a purity of 99.5% by weight. The product was stabilized with 7 mg of MEHQ. The color number was 145 Hazen.

EXAMPLE 2: NORBORNYL ACRYLATE WITH INITIAL CHARGE OF DIOXANE 5 ml of dioxane were initially charged in a 250 ml four-neck round-bottom flask with reflux condenser, magnetic stirrer, thermometer, dropping funnel and air inlet. 0.5 ml of boron trifluoride dimethyl etherate was added. A solution of 40 g of norbornene, 0.1 g of MEHQ and 61.5 g of acrylic acid was added dropwise with introduction of air (1 l/h), with stirring (280 rpm) and heating, such that the internal temperature was 90-92° C. The mixture was stirred at temperature for a further 1 h. The reaction mixture that had cooled to room temperature was admixed with 300 ml of dichloromethane and with 200 ml of 12.5% NaOH solution and extracted. The phases were separated, the organic phase was extracted once more with 100 ml of 12.5% NaOH solution and concentrated after phase separation. 65.5 g of product (92.8% yield) were obtained with a purity of 99.5% by weight. The product was stabilized with 7 mg of MEHQ. The color number was 74 Hazen.

EXAMPLE 3: NORBORNYL METHACRYLATE WITH INITIAL CHARGE OF DIOXANE 7.5 ml of dioxane were initially charged in a 500 ml four-neck round-bottom flask with reflux condenser, magnetic stirrer, thermometer, dropping funnel and air inlet. 0.9 ml of boron trifluoride dimethyl etherate was added. A solution of 75.1 g of norbornene, 0.22 g of MEHQ and 138 g of methacrylic acid was added dropwise with introduction of air (1 l/h), stirring (500 rpm) and heating, such that the internal temperature was 90-95° C. The mixture was stirred at temperature for a further 1 h. The reaction mixture that had cooled to room temperature was admixed with 200 ml of dichloromethane and with 300 ml of 12.5% NaOH solution and extracted. The phases were separated, the organic phase was extracted once more with 100 ml of 12.5% NaOH solution and another two times after phase separation with 100 ml each time of water, the phases were each separated and the organic phase was concentrated. 136 g of product (94.7% yield) were obtained with a purity of 99.7% by weight. The product was stabilized with 13.6 mg of MEHQ. The color number was 136 Hazen.

EXAMPLE 4: NORBORNYL METHACRYLATE WITH INITIAL CHARGE OF NORBORNYL METHACRYLATE 5 g of norbornyl methacrylate were initially charged in a 500 ml four-neck round-bottom flask with reflux condenser, magnetic stirrer, thermometer, dropping funnel and air inlet. 1 ml of boron trifluoride dimethyl etherate was added. A solution of 75.1 g of norbornene, 0.22 g of MEHQ and 137.5 g of methacrylic acid was added dropwise with introduction of air (1 l/h), stirring (500 rpm) and heating, such that the internal temperature was 95-97° C. The mixture was stirred at temperature for a further 1 h. The reaction mixture that had cooled to room temperature was admixed with 200 ml of dichloromethane and with 300 ml of 12.5% NaOH solution and extracted. The phases were separated, the organic phase was extracted once more with 100 ml of 12.5% NaOH solution and another two times after phase separation with 100 ml each time of water, the phases were each separated and the organic phase was concentrated. 145 g of product (97.6% yield) were obtained with a purity of 99.9% by weight. The product was stabilized with 14.6 mg of MEHQ. The color number was 206 Hazen.

EXAMPLE 5: NORBORNYL METHACRYLATE WITH INITIAL CHARGE OF METHACRYLIC ACID 202 g of methacrylic acid, 0.56 g of MEHQ and 2.5 ml of boron trifluoride dimethyl etherate were initially charged in a 2 l four-neck round-bottom flask with Normag attachment, magnetic stirrer, thermometer, dropping funnel and air inlet. The mixture was heated with stirring (500 rpm) and introduction of air (1 l/h), and a solution of 275 g of norbornene and 100 g of methacrylic acid was added dropwise, such that the internal temperature was 93-97° C.

After addition was complete, stirring was continued for a further 3.5 h. Excess acid was distilled off under reduced pressure. The reaction mixture that had cooled to room temperature was extracted with 30% NaOH (105 g) and the phases were separated. Two further extractions and phase separations followed, with 250 ml of water and 50 ml of saturated sodium chloride solution and also 100 ml of water and 150 ml of saturated sodium chloride solution.

The organic phase was admixed with 50 mg of MEHQ, concentrated at 60° C. to 5.5 mbar in order to remove traces of water and any methacrylic acid, and subsequently filtered. 493.4 g of product (yield 93.7%) were obtained with a purity of 99.4% by weight. The color number was 81 Hazen.

EXAMPLE 6: NORBORNYL METHACRYLATE WITH INITIAL CHARGE OF METHACRYLIC ACID 54.9 g of methacrylic acid and 26 mg of MEHQ were initially charged in a 500 ml four-neck round-bottom flask with reflux condenser, magnetic stirrer, thermometer, heatable dropping funnel and air inlet. 0.65 ml of boron trifluoride dimethyl etherate was added. 50 molten norbornene was added dropwise with introduction of air (1 l/h), stirring (500 rpm) and heating, such that the internal temperature was 85-105° C. The mixture was stirred at 94° C. for a further 5.8 h. The reaction mixture that had cooled to room temperature was admixed with 200 ml of dichloromethane and with 20 g of 50% NaOH solution and extracted. The phases were separated, the organic phase was extracted two more times with 100 ml each time of 12.5% aqueous sodium chloride solution, the phases were each separated and the organic phase was concentrated at 60° C. to 5.5 mbar in order to remove traces of water and any methacrylic acid. After filtration, 92 g of product (96.1% yield) were obtained with a purity of 99.6% by weight. The color number was 150 Hazen.

EXAMPLE 7: NORBORNYL METHACRYLATE WITH INITIAL CHARGE OF METHACRYLIC ACID 258 g of methacrylic acid, 0.78 g of MEHQ and 2.5 ml of boron trifluoride dimethyl etherate were initially charged in a 2 l four-neck round-bottom flask with Normag attachment, magnetic stirrer, thermometer, dropping funnel and air inlet. The mixture was heated with stirring (500 rpm) and introduction of air (1 l/h), and a solution of 275 g of norbornene and 245 g of methacrylic acid was added dropwise, such that the internal temperature was 92-97° C.

After addition was complete, stirring was continued for a further 3 h. Excess acid was partially distilled off under reduced pressure. The reaction mixture that had cooled to room temperature was extracted with 30% NaOH (122 g) and the phases were separated. Two further extractions and phase separations followed with in each case 250 ml of water and 50 ml of saturated sodium chloride solution.

The organic phase was concentrated at 60° C. to 5.5 mbar in order to remove traces of water and any methacrylic acid, and subsequently filtered. 508.5 g of product (yield 96.6%) were obtained with a purity of 99.8% by weight. The end product was stabilized with 51 mg of MEHQ. The color number was 39 Hazen.

COMPARATIVE EXAMPLE 1: NORBORNYL ACRYLATE WITH INITIAL CHARGE OF NORBORNENE 40 g of norbornene were initially charged in a 250 ml four-neck round-bottom flask with reflux condenser, magnetic stirrer, thermometer, dropping funnel and air inlet, and melted. 0.1 g of MEHQ and 0.5 ml of boron trifluoride dimethyl etherate were added. 61.5 g of acrylic acid were added dropwise at an internal temperature of initially 50° C. After dropwise addition complete, the internal temperature was 76° C. The temperature was raised to 90° C. and stirring performed for a further 5 h. The reaction mixture that had cooled to room temperature was admixed with 300 ml of dichloromethane and with 250 ml of 8% NaHCO$_3$ solution and extracted. A further 30 g of NaHCO$_3$ were added. The phases were separated, the organic phase was extracted once more with 250 ml of 8% NaHCO₃ solution and concentrated after phase separation. 55.3 g of product were obtained with a purity of 70.8% by weight.

EXAMPLE 2: NORBORNYL ACRYLATE WITH INITIAL CHARGE OF ACRYLIC ACID 76.5 g of acrylic acid and 52 mg of MEHQ were initially charged in a 500 ml four-neck round-bottom flask with reflux condenser, magnetic stirrer, thermometer, heatable dropping funnel and air inlet. 0.65 ml of boron trifluoride dimethyl etherate was added. 50 molten norbornene was added dropwise with introduction of air (1 l/h), stirring (500 rpm) and heating, such that the internal temperature was 85-100° C. The mixture was stirred at 94° C. for a further 5.3 h. The reaction mixture that had cooled to room temperature was admixed with 20 g of 50% NaOH solution and extracted. The phases were separated, the organic phase was extracted two more times with 100 ml each time of 12.5% aqueous sodium chloride solution, the phases were each separated and the organic phase was concentrated at 60° C. to 5.5 mbar in order to remove traces of water and any acrylic acid. After filtration, 91 g of product (95.1% yield) were obtained with a purity of 97% by weight. The color number was 34 Hazen.

The invention claimed is:

1. A method for preparing norbornyl (meth)acrylate by reacting norbornene with (meth)acrylic acid in the presence of boron trifluoride as catalyst, wherein
   a) boron trifluoride is initially charged in (meth)acrylic acid,
   b) the initial charge is heated to a temperature of 75 to 110° C.,
   c) norbornene is added and
   d) the norbornyl (meth)acrylate obtained is isolated from the reaction mixture.

2. A method for preparing norbornyl (meth)acrylate by reacting norbornene with (meth)acrylic acid in the presence of boron trifluoride as catalyst, wherein
   a) boron trifluoride is initially charged in an organic solvent,
   b) the initial charge is heated to a temperature of 75 to 110° C.,
   c) a mixture comprising norbornene and (meth)acrylic acid is added and
   d) the norbornyl (meth)acrylate obtained is isolated from the reaction mixture.

3. The method according to claim 1, wherein boron trifluoride is used in an amount of 0.1 to 5 mole percent, based on the amount of norbornene.

4. The method according to claim 1, wherein boron trifluoride is used in an amount of 0.5 to 1.5 mole percent, based on the amount of norbornene.

5. The method according to claim 1, wherein boron trifluoride is used in the form of the diethyl etherate, dimethyl etherate or any desired mixture of these.

6. The method according to claim 2, wherein the organic solvent is ether, norbornyl (meth)acrylate, (meth)acrylic acid or any mixture of these.

7. The method according to claim 6, wherein the organic solvent is (meth)acrylic acid.

8. The method according to claim 1, wherein the reaction takes place in the presence of a stabilizer and the stabilizer is phenothiazine, one or more phenolic compounds, one or more N-oxyls or any mixture of these.

9. The method according to claim 8, wherein the stabilizer is para-methoxyphenol (MEHQ).

10. The method according to claim 1, wherein the reaction takes place in the presence of oxygen.

11. The method according to claim 1, wherein (meth) acrylic acid is used in an amount of 100 to 1000 mole percent, based on the amount of norbornene.

12. The method according to claim 1, wherein the isolation of norbornyl (meth)acrylate from the reaction mixture comprises one or more extraction steps.

13. The method according to claim 1, wherein the isolation of norbornyl (meth)acrylate from the reaction mixture comprises separating off the more volatile compounds by distillation.

14. The method according to claim 12, wherein the norbornyl (meth)acrylate thus isolated has a purity of at least 99 percent by weight.

* * * * *